United States Patent [19]

Köppe et al.

[11] 3,969,512

[45] July 13, 1976

[54] N,N'BIS-(3-PHENOXY-2-HYDROXY-PROPYL)-ALKYLENEDIAMINES AND SALTS THEREOF

[75] Inventors: Herbert Köppe; Helmut Stahle; Werner Kummer; Gojko Muacevic; Werner Traunecker, all of Ingelheim am Rhein, Germany

[73] Assignee: Boehringer Ingelheim GmbH, Ingelheim am Rhein, Germany

[22] Filed: Feb. 10, 1975

[21] Appl. No.: 548,366

Related U.S. Application Data

[62] Division of Ser. No. 336,269, Feb. 27, 1973, Pat. No. 3,888,898.

[30] Foreign Application Priority Data

Mar. 6, 1972 Germany............................ 2210620
Dec. 11, 1972 Germany............................ 2260444

[52] U.S. Cl............................. 424/330; 260/570.7
[51] Int. Cl.²................ A61K 31/135; C07C 93/06
[58] Field of Search.............. 424/330; 260/570.7 R, 260/570.7 OH

[56] References Cited
UNITED STATES PATENTS

| | | | |
|---|---|---|---|
| 3,332,997 | 7/1967 | Renner et al. .................. | 260/570.7 |
| 3,742,023 | 6/1973 | Koppe et al. ..................... | 424/330 |
| 3,769,430 | 10/1973 | Schromm et al................ | 424/330 |
| 3,888,829 | 6/1975 | Bastian et al. ..................... | 424/330 |

FOREIGN PATENTS OR APPLICATIONS

| | | | |
|---|---|---|---|
| 1,294,955 | 1/1966 | Germany ......................... | 260/570.7 |
| 6,600,177 | 7/1967 | Netherlands..................... | 260/570.7 |

Primary Examiner—Donald B. Moyer
Attorney, Agent, or Firm—Hammond & Littell

[57] ABSTRACT

Compounds of the formula

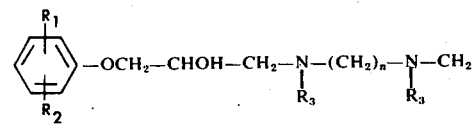

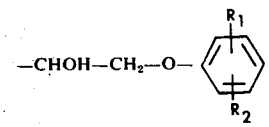

wherein $R_1$ is allyl, allyloxy or chlorine,
$R_2$ is hydrogen or methyl,
$R_3$ is hydrogen, alkyl of 1 to 5 carbon atoms or benzyl, and
$n$ is an integer from 2 to 6, inclusive, provided, however, that when $R_1$ is allyl or allyloxy, $R_2$ is hydrogen; and their non-toxic, pharmacologically acceptable acid addition salts; the compounds as well as their salts are useful as $\beta$-adrenergic blocking agents and hypotensives.

11 Claims, No Drawings

N,N'-BIS-(3-PHENOXY-2-HYDROXY-PROPYL)-ALKYLENEDIAMINES AND SALTS THEREOF

This is a division of copending application Ser. No. 336,269, filed Feb. 27, 1973, now U.S. Pat. No. 3,888,898 granted June 10, 1975.

This invention relates to novel N,N'-bis-(3-phenoxy-2-hydroxy-n-propyl)-alkylenediamines and their non-toxic acid addition salts, as well as to methods of preparing these compounds.

More particularly, the present invention relates to a novel class of compounds represented by the formula

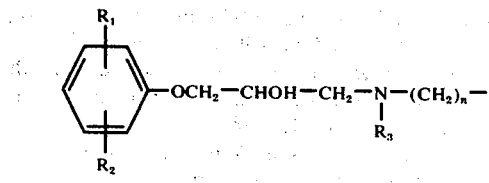

wherein $R_1$ is allyl, allyloxy or chlorine,
$R_2$ is hydrogen or methyl,
$R_3$ is hydrogen, alkyl of 1 to 5 carbon atoms or benzyl; and
$n$ is an integer from 2 to 6, inclusive,
provided, however, that when $R_1$ is allyl or allyloxy, $R_2$ is hydrogen; and their non-toxic, pharmacologically acceptable acid addition salts.

The compounds embraced by formula I above may be prepared by the following methods:

Method A

By reacting a compound of the formula

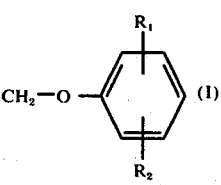 (II)

wherein $R_1$ and $R_2$ have the meanings defined above, and Z is

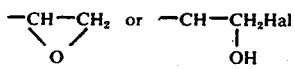

(Hal = halogen), with an alkylenediamine of the formula $R_3HN-(CH_2)_n-NHR_3$ (III)

wherein $R_3$ and $n$ have the meanings defined above.

Method B

By reacting a compound of the formula

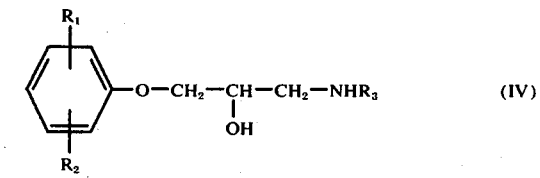 (IV)

wherein $R_1$ to $R_3$ have the meanings previously defined, with an alkylenedihalide of the formula $Hal-(CH_2)_n-Hal$ (V)

wherein $n$ and Hal have the above-defined meanings. The reaction proceeds in 2 steps with intermediate formation of a compound of the formula

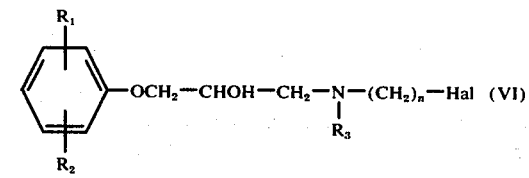

wherein $R_1$ to $R_4$, $n$ and Hal have the meanings defined above. It is also possible to produce a compound of the formula I directly from a compound of the formula VI by reacting it with a compound of the formula IV.

Method C

By splitting off a protective group from a bis-tertiary amine of the formula

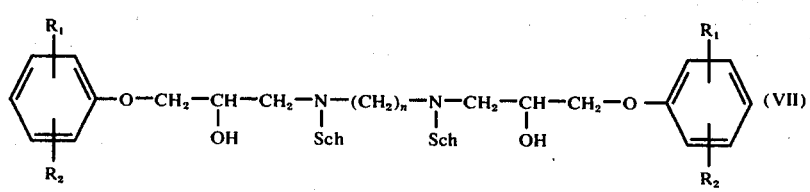

wherein $R_1$, $R_2$ and $n$ have the above-defined meanings, and Sch is an easily removable amino-protective group, such as benzyl. This method leads to compounds of the formula I wherein $R_3$ is hydrogen.

Most of the starting compounds of the formulas II to VII are known. Those which are not known may be prepared by conventional methods. Thus, an epoxide of the formula II may be obtained by reacting the corresponding phenol of the formula

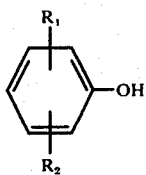

(VIII)

where in $R_1$ and $R_2$ have the meanings previously defined, or a salt thereof (preferably an alkali metal salt) with epichlorohydrin; a halohydrin of the formula II may be obtained by cleavage of the epoxide with the corresponding hydrohalic acid.

A compound of the formula III, wherein $R_3$ is alkyl, may be obtained from the corresponding compound of the formula III, wherein $R_3$ is hydrogen, by treatment with a conventional alkylating agent $R_3$—X (X = radical of a reactive ester, such as halogen or toluenesulfonyloxy). Secondary alkyl groups may also be obtained by reductive amination with the corresponding ketone, such as acetone, and $NaBH_4$.

A compound of the formula IV may be obtained by reacting a compound of the formula II with an amine of the formula $NH_2$—$R_3$, where $R_3$ has the meanings defined above.

A compound of the formula V is obtainable from a corresponding alkane-diol HO—$(CH_2)_n$—OH by reaction with a conventional halogenating agent, such as $SOCl_2$ or $PCl_5$.

A compound of the formula VI may be prepared by reacting a corresponding haloalkylamine of the formula $R_4NH$—$(CH_2)_n$—Hal     (IX)

wherein $R_4$, n and Hal have the previously defined meanings, with a compound of the formula II.

A compound of the formula VII is advantageously prepared by reacting a compound of the formula II with a diamine of the formula SchHN—$(CH_2)_n$—NHSch     (X)

wherein Sch and n have previously defined meanings. A compound of the formula X may be produced from a compound of the formula III wherein $R_3$ is hydrogen by reacting the latter with a conventional reagent for forming protective groups, such as benzyl bromide, acetyl chloride or carbobenzoxy chloride.

The compounds embraced by formula I possess two asymmetric carbon atoms and occur therefore as racemates, as well as in the form of optical antipodes. The racemates may be separated with the aid of optically active auxiliary acids, such as di-O, O-p-toluyl-D-tartaric acid, into their optical antipode components.

The compounds of the formula I, both in the form of racemates or optical antipodes, form acid addition salts with inorganic or organic acids. Examples of non-toxic, pharmacologically acceptable acid addition salts are those formed with hydrochloric acid, hydrobromic acid, sulfuric acid, maleic acid, lactic acid, methanesulfonic acid, oxalic acid, tartaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

N,N'-Bis-[2-hydroxy-3-(2'-allyl-phenoxy)-1-propyl]-ethylenediamine . 2 HCl by method A 19 gm (0.1 mol) of 1-(2'-allyl-phenoxy)-2,3-epoxy-propane were dissolved in 150 ml of ethanol, 3 gm (0.05 mol) of ethylenediamine were added, and the mixture was refluxed for 2 hours. After having cooled off, the solvent was distilled off, and the residue was dissolved in dilute HCl. Insoluble matter was separated, and the aqueous solution was made alkaline with NaOH. The precipitated basic components were extracted with ether, and the organic phase was separated, washed with water and dried over $MgSO_4$. After having distilled off the ether, 13 gm of residue remained, which were dissolved in little ethanol and admixed with ethereal HCl. The precipitate was recrystallized twice from methanol, subsequently digested with water, vacuum-filtered off and dried, yielding 4.5 gm of the compound of the formula

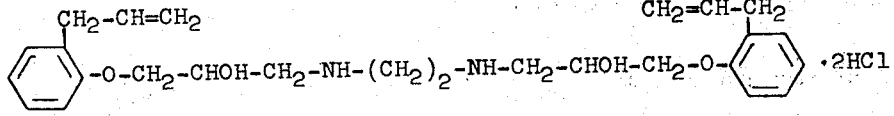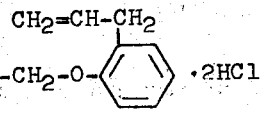

which had a melting point of 248°–251°C.

EXAMPLE 2

N,N'-Bis-[2'-hydroxy-3'-(2''-allyloxy-phenoxy)-1'-propyl]-1,2-ethylenediamine . 2 HCl by method A 10.3 gm (0.05 mol) of 1-(2'-allyloxy-phenoxy)-2,3-epoxy-propane and 1.5 gm (0.025 mol) of ethylenediamine were refluxed in 100 ml of ethanol for 2 hours. After having distilled off the solvent, the solid residue (12.6 gm) was recrystallized from ethyl acetate by addition of petroleum ether. The base thus obtained was dissolved in methanol, and ethereal HCl was added. The hydrochloride which crystallized out was recrystallized once more from methanol, yielding 2.4 gm of the compound of the formula

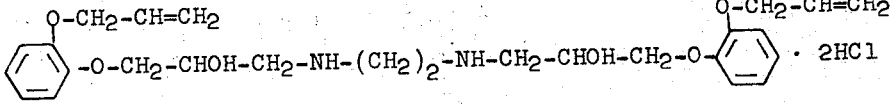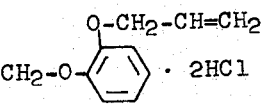

which had a melting point of 188°–190°C.

EXAMPLE 3

N,N'-Bis-[1-(2''-chloro-5''-methyl-phenoxy)-2'-hydroxy-propyl-3']-butylene-1,4-diamine . 2 HCl by method A 8.45 gm (0.042 mol) of 1-(2'-chloro-5'-methyl-phenoxy)-2,3-epoxy-propane were dissolved in 75 ml of ethanol, and 1.85 gm of (0.021 mol) of butylenediamine-1,4 were added. The mixture was refluxed for two hours, and was then evaporated to dryness. The residue was triturated with ether, the solid components were recrystallized from ethyl acetate by addition of ether, and the colorless crystals were dissolved in methanol. The solution was acidified with ethereal hydrochloric acid, and the colorless crystalline precipitate formed thereby was collected, yielding 2.5 gm of the compound of the formula

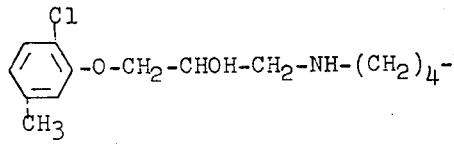-O-CH$_2$-CHOH-CH$_2$-NH-(CH$_2$)$_4$-NH-CH$_2$-CHOH-CH$_2$-O-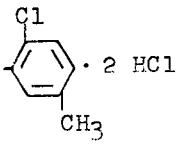 . 2 HCl which had a melting point of 233°–235°C.

EXAMPLE 4

N,N'-Bis-[1'-(2''-chloro-5''-methyl-phenoxy)-2'-hydroxy-propyl -3']-1,2-ethylenediamine . 2 HCl by method A 10 gm (0.05 mol) of 1-(2'-chloro-5'-methyl-phenoxy)-2,3-epoxy-propane were dissolved with 1.5 gm (0.025 mol) of ethylenediamine in 100 ml of ethanol. After refluxing the solution for 2 hours, it was cooled with ice water, whereby the reaction product crystallized out which was collected by vacuum filtration and recrystallized from dimethylformamide. The colorless base, which melted at 156° to 160°C, was dissolved in methanol and ethereal HCl was added. The precipitate formed thereby was collected, yielding 3.2 gm of the compound named in the heading, which had a melting point of 255°–260°C.

EXAMPLE 5

N,N'-Bis-[1'-(2''-chloro-5''-methyl-phenoxy)-2'-hydroxy-propyl-3']-N,N'-bis-isopropyl-hexamethylene-1,6-diamine . 2 HCl by method B 16.8 gm (0.065 mol) of 1-(2'-chloro-5'methyl-phenoxy)-3-isopropylamino-propanol-(2) were dissolved in 100 ml of ethanol, 7 gm of NaHCO$_3$ were added, and then 7.92 gm (0.0325 mol) of 1,6-dibromohexane were added dropwise. The resulting mixture was refluxed for 10 hours. Subsequently, after distilling off the solvent, the residue was acidified with HCl, the aqueous phase extracted with ether and made alkaline with NaOH. The precipitate was taken up in chloroform, and the solution was washed with water. After drying over MgSO$_4$, the CHCl$_3$ was distilled off, and the residual mixture of bases was separated by column-chromatography. The pure substance (8.4 gm) was dissolved in a little ethanol, alcoholic HCl and ether were added, and the oil which separated out was dissolved in acetonitrile. Upon addition of ether, a colorless crystalline substance separated out which was recrystallized from ethanol by addition of ether, yielding 6.8 gm of the compound named in the heading, which had a melting point of 187°–189°C.

EXAMPLE 6

N,N'-Bis-[1'-(2''-chloro-5''-methyl-phenoxy)-2'-hydroxypropyl-3']-N,N'-bis-methyl-hexamethylene-1,6-diamine . 2 HCl by method C 2.068 gm (0.004 mol) of N,N'-bis-[1'-(2''-chloro-5''-methyl-phenoxy)-2'-hydroxypropyl-3']-hexamethylene-1,6-diamine were mixed with 4.6 gm (0.1 mol) of formic acid and 6 ml of 30% formalin solution, and the mixture was heated to 90°C. After the evolution of CO$_2$ had started, the temperature was held at 90°C for 2 hours. The cooled solution was made alkaline with NaOH, extracted with CHCl$_3$, and the organic phase was washed with H$_2$O and dried over Na$_2$SO$_4$. After distilling off the chloroform, 2.2 gm of a residue were obtained which was dissolved in acetonitrile, and the solution was acidified with alcoholic HCl. The crystalline product formed thereby was recrystallized from methanol by addition of ether, yielding 1.8 gm of the compound named in the heading, which had a melting point of 185°–189°C.

EXAMPLE 7

N,N'-Bis-[1'-(2''-chloro-5''-methyl-phenoxy)-2'-hydroxypropyl-3']-N,N'-bis-benzyl-hexamethylene-1,6-diamine . 2 HCl by method A 15 gm (0.075 mol) of 1-(2'-chloro-5'-methyl-phenoxy) -2,3-epoxy-propane were dissolved in 200 ml of absolute ethanol, 10.4 gm (0.035 mol) of 1,6-dibenzylamino-hexane were added, and the mixture was refluxed for 2 hours. After distilling off the solvent, the residue was dissolved in acetonitrile, and the solution was acidified with alcoholic HCl. The precipitated crystals were recrystallized from methanol by addition of ether, yielding 19.4 gm of the compound of the formula

-O-CH$_2$-CHOH-CH$_2$-N-(CH$_2$)$_6$-N-CH$_2$-CHOH-CH$_2$-O-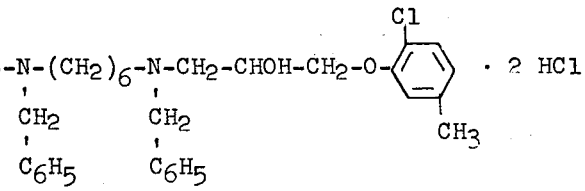 . 2 HCl which had a melting point of 185°–188°C.

EXAMPLE 8

N,N'-Bis-[1'-(2''-chloro-5''-methyl-phenoxy)-2'-hydroxypropyl-3']-hexamethylene-1,6-diamine . 2 HCl 14.5 gm (0.019 mol) of N,N'-bis-[1'-(2''-chloro-5-methyl-phenoxy)-2'-hydroxy-propyl-3']-N,N'-dibenzyl-hexamethylene-1,6-diamine . 2 HCl were hydrogenated over palladized coal in 200 ml of methanol at 6 atm./60°C until absorption of the theoretical quantity of hydrogen. After separation of the catalyst, the solvent was distilled off, and the solid residue was recrystallized twice from ethanol by addition of ether. 5.6 gm of the compound named in the heading, which had a melting point of 207°–210°C, were obtained.

The compounds embraced by formula I and their non-toxic, pharmacologically acceptable acid addition salts have useful pharmacodynamic properties. More particularly, the compounds of the present invention exhibit β-adrenergic receptor blocking and hypotensive activities in warm-blooded animals, such as guinea pigs, cats and dogs.

Of particular significance is the cardio-selective blocking action upon the β-receptors of the heart, i.e. the so-called $\beta_1$-activity, which the compounds according to the present invention produce.

Therefore, the compounds embraced by formula I and their non-toxic, pharmacologically acceptable acid addition salts are useful for the treatment or prophylaxis of disorders of the heart or coronary vessels as well as hypertension in warm-blooded animals.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. The effective single dosage unit range of the compounds according to the present invention is from 0.0016 to 5.0 mgm/kg body weight. The preferred oral dosage unit range is 0.016 to 1.0 mgm/kg body weight, and the preferred parenteral dosage unit range is 0.0016 to 0.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 9

Tablets

The tablet composition is compounded from the following ingredients:

| | |
|---|---:|
| N,N'-bis-[2'-hydroxy-3'-(2''-allyloxy-phenoxy)-1'-propyl]-ethylenediamine . 2 HCl | 20.0 parts |
| Corn starch | 164.0 parts |
| Calcium phosphate | 240.0 parts |
| Magnesium stearate | 1.0 parts |
| | 425.0 parts |

Preparation:

The individual ingredients are intimately admixed with each other, and the mixture is granulated in the conventional way. Then, the granulate is compressed into 425 mgm-tablets each of which contains 20 mgm of the ethylenediamine compound and is an oral dosage unit composition with effective β-adrenergic receptor blocking and hypotensive action.

EXAMPLE 10

Gelatin capsules

The capsule filler composition is compounded from the following ingredients:

| | |
|---|---:|
| N,N'-bis-2'-hydroxy-3'-(2''-allyl-phenoxy)-1'-propyl]-ethylenediamine . 2 HCl | 25.0 parts |
| Corn starch | 175.0 parts |
| | 200.0 parts |

Preparation:

The ingredients are intimately admixed with each other, and 200 mgm portions of the mixture are filled into gelatin capsules of suitable size. Each capsule contains 25 mgm of the ethylenediamine compound and is an oral dosage unit composition with effective β-adrenergic receptor blocking and hypotensive action.

EXAMPLE 11

Hypodermic solution

The solution is compounded from the following ingredients:

| | |
|---|---:|
| N,N'-bis-[2'-hydroxy-1'-(2''-chloro-5''-methyl-phenoxy)-3'-propyl]-1,6-hexamethylenediamine . 2 HCl | 1.5 parts |
| Sodium salt of EDTA (ethylenediamine tetraacetic acid) | 0.2 parts |
| Distilled water  q.s.ad | 100.0 parts |

Preparation:

The active ingredient and the EDTA salt are dissolved in a sufficient amount of distilled water, and the solution is diluted with water to the indicated weight. The solution is filtered until free from suspended particles and filled into 1 cc-ampules under aseptic conditions. Finally, the ampules are sterilized and sealed. Each ampule contains 15 mgm of the hexamethylenediamine compound, and the contents thereof are an injectable dosage unit composition with effective β-adrenergic receptor blocking and hypotensive action.

EXAMPLE 12

Coated sustained-release tablets

The tablet core composition is compounded from the following ingredients:

| | |
|---|---:|
| N,N'-bis-[1'-(2''-chloro-5''-methyl-phenoxy)-2'-hydroxypropyl-3']-1,2-ethylenediamine dihydrochloride | 25.0 parts |
| Carboxymethyl cellulose (CMC) | 295.0 parts |
| Stearic acid | 20.0 parts |
| Celluloseacetate phthalate (CAP) | 40.0 parts |
| | 380.0 parts |

Preparation:

The active ingredients, the CMC and the stearic acid are intimately admixed with each other, and the mixture is granulated in the conventional way, using a solution of the CAP in 200 mgm of an ethanol/ethylacetate mixture as the moistener. Then, the granulate is compressed into 380 mgm-tablet cores, which are subsequently coated with a mixture of sugar and polyvinylpyrrolidone. Each coated tablet contains 25 mgm of the ethylenediamine compound and is an oral dosage unit composition with effective β-adrenergic receptor blocking and hypotensive action.

Dosage unit compositions containing a compound of the present invention as an active ingredient may, in addition, also contain one or more other active ingredients with different pharmacological activities, such as coronary dilators, sympathomimetics and tranquilizers, as illustrated by the following examples.

EXAMPLE 13

Coated sustained-release tablets

The tablet core composition is compounded from the following ingredients:

| | |
|---|---|
| N,N'-bis-[2'-hydroxy-3'-(2''-allyloxy-phenoxy)-1'-propyl]-1,6-hexamethylenediamine . 2 HCl | 25.0 parts |
| Oxazepam | 20.0 parts |
| Carboxymethyl cellulose (CMC) | 295.0 parts |
| Stearic acid | 20.0 parts |
| Celluloseacetate phthalate (CAP) | 40.0 parts |
| | 400.0 parts |

Preparation:

The tablets are manufactured in a manner analogous to that described in Example 12. Each tablet contains 25 mgm of the hexamethylenediamine compound and 20 mgm of oxazepam, and is an oral dosage unit composition with effective β-adrenergic receptor blocking, hypotensive and tranquilizing action.

EXAMPLE 14

Tablets

The tablet composition is compounded from the following ingredients:

| | |
|---|---|
| N,N'-bis-[2'-hydroxy-3'-(2''-allyl-phenoxy)-1'-propyl]-ethylenediamine . 2 HCl | 35.0 parts |
| 2,6-bis-(diethanolamino)-4,8-dipiperidino-pyrimido-[5,4-d]-pyrimidine | 75.0 parts |
| Lactose | 164.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10.0 parts |
| | 500.0 parts |

Preparation:

The active ingredients are intimately admixed with the lactose, the corn starch, the colloidal silicic acid and the polyvinylpyrrolidone, and the mixture is granulated in the usual way, using an aqueous solution of the soluble starch as the moistener. The granulate is admixed with the magnesium stearate, and the composition is compressed into 500 mgm-tablets in a conventional tablet making machine. Each tablet contains 35 mgm of the hexamethylenediamine compound and 75 mg of the pyrimidopyrimidine compound, and is an oral dosage unit composition with effective β-adrenergic receptor blocking, hypotensive and coronary dilating action.

Analogous results are obtained when any one of the other compounds embraced by formula I or a non-toxic acid addition salt thereof was substituted for the particular alkylenediamine derivative in Examples 9 through 14. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

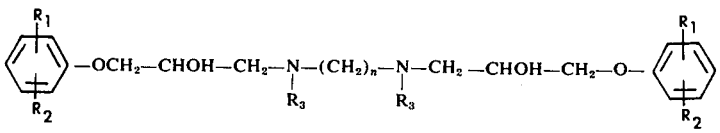—OCH$_2$—CHOH—CH$_2$—N—(CH$_2$)$_n$—N—CH$_2$—CHOH—CH$_2$—O—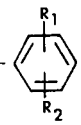

wherein R$_1$ is allyl, allyloxy or chlorine,
R$_2$ is hydrogen or methyl,
R$_3$ is hydrogen, alkyl of 1 to 5 carbon atoms or benzyl, and
n is an integer from 2 to 6, inclusive,
provided, however, that when R$_1$ is allyl or allyloxy, R$_2$ is hydrogen; or a non-toxic, pharmacologically acceptable acid addition salt thereof.

2. A compound of claim 1, which is N,N'-bis-[2-hydroxy-3-(2'-allyl-phenoxy)-1-propyl]-ethylenediamine or a non-toxic, pharmacologically acceptable acid addition salt thereof.

3. A compound of claim 1, which is N,N'-bis-[2'-hydroxy-3'-(2''-allyloxy-phenoxy)-1'-propyl]-ethylenediamine or a non-toxic, pharmacologically acceptable acid addition salt thereof.

4. A compound of claim 1, which is N,N'-bis-[1'-(2'λ'-chloro-5''-methyl-phenoxy)-2'-hydroxy-propyl-3']-butylene-1,4-diamine or a non-toxic, pharmacologically acceptable acid addition salt thereof.

5. A compound of claim 1, which is N,N'-bis-[1'-(2'λ'-chloro-5''-methyl-phenoxy)-2'-hydroxy-propyl-3']-ethylenediamine or a non-toxic, pharmacologically acceptable acid addition salt thereof.

6. A compound of claim 1, which is N,N'-bis-[1'-(2'λ'-chloro-5''-methyl-phenoxy)-2'-hydroxy-propyl-3']-N,N'-bis-isopropyl-1,6-hexamethylenediamine or a non-toxic, pharmacologically acceptable acid addition salt thereof.

7. A compound of claim 1, which is N,N'-bis-[1'-(2'λ'-chloro-5''-methyl-phenoxy)-2'-hydroxy-propyl-3']-N,N'-bis-methyl-1,6-hexamethylenediamine or a non-toxic, pharmacologically acceptable acid addition salt thereof.

8. A compound of claim 1, which is N,N'-bis-[1'-(2'λ'-chloro-5''-methyl-phenoxy)-2'-hydroxy-propyl-3']-N,N'-bis-benzyl-1,6-hexamethylenediamine or a non-toxic, pharmacologically acceptable acid addition salt thereof.

9. A compound of claim 1, which is N,N'-bis-[1'-(2'λ'-chloro-5''-methyl-phenoxy)-2'-hydroxy-propyl-3']-1,6-hexamethylenediamine or a non-toxic, pharmacologically acceptable acid addition salt thereof.

10. A β-adrenolytic and hypotensive pharmaceutical dosage unit composition consisting essentially of an inert pharmaceutical carrier and an effective β-adrenergic receptor blocking and hypotensive amount of a compound of claim 1.

11. The method of blocking the β-adrenergic receptors and lowering the blood pressure of a warm-blooded animal in need of such treatment, which comprises perorally or parenterally administering to said animal an effective β-adrenergic receptor blocking and hypotensive amount of a compound of claim 1.

* * * * *

UNITED STATES PATENT OFFICE
CERTIFICATE OF CORRECTION

Patent No. 3,969,512      Dated July 13, 1976

Inventor(s) HERBERT KÖPPE, HELMUT STAHLE: WERNER KUMMER, GOJKO MUACEVIC and WERNER TRAUNECKER It is certified that error appears in the above-identified patent and that said Letters Patent are hereby corrected as shown below:

Col. 10, lines 33, 37, 40, 45, 50, 54    "(2'γ" should read -- (2" --

Col. 10, lines 34, 38, 41, 46, 51, 55    "'-chloro-" should read -- -chloro- --

Signed and Sealed this

Second Day of November 1976

[SEAL]

Attest:

RUTH C. MASON
*Attesting Officer*

C. MARSHALL DANN
*Commissioner of Patents and Trademarks*